United States Patent
Eichenhofer et al.

[11] 3,965,097
[45] June 22, 1976

[54] PRODUCTION OF KETAZINES

[75] Inventors: Kurt-Wilhelm Eichenhofer, Leverkusen; Reinhard Schliebs, Cologne, both of Germany

[73] Assignee: Bayer Aktiengesellschaft, Leverkusen, Germany

[22] Filed: Mar. 6, 1975

[21] Appl. No.: 556,036

[30] Foreign Application Priority Data
Mar. 27, 1974 Germany............................ 2414802

[52] U.S. Cl.......................... 260/240 G; 260/566 B
[51] Int. Cl.²..................................... C07C 109/00
[58] Field of Search..................... 260/566 B, 240 G

[56] References Cited
UNITED STATES PATENTS

| | | | |
|---|---|---|---|
| 2,870,206 | 1/1959 | Meyer et al. | 260/566 B |
| 2,894,032 | 7/1959 | Rudner | 260/566 B |

OTHER PUBLICATIONS
Chem. Ber. 97, 2521 (1964).
Chem. Ber. 100, 2600 (1967).
Z. Chem. 3, 190 (1963).

*Primary Examiner*—Gerald A. Schwartz
*Attorney, Agent, or Firm*—Burgess, Dinklage & Sprung

[57] ABSTRACT

A process for the production of a ketazine of the general formula

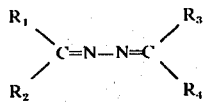

in which
$R_1$, $R_2$, $R_3$ and $R_4$ each independently is an alkyl, cycloalkyl or aralkyl radical with up to 12 carbon atoms; or an optionally substituted aryl radical with up to 10 carbon atoms, at most two of the radicals $R_1$, $R_2$, $R_3$ and $R_4$ being aryl radicals, or $R_1 + R_2$ and $R_3 + R_4$ individually is an alkylene radical with from 5 to 10 carbon atoms, which comprises reacting a 3,3-diorganyl oxaziridine of the formula

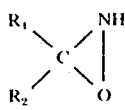

with ammonia in the presence of a ketone of the formula

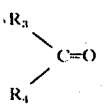

Advantageously the oxaziridine is 3,3-dimethyl oxaziridine, 3,3-methyl ethyl oxaziridine, 3,3-diethyl oxaziridine or 3,3-pentamethylene oxaziridine, the ketone is acetone, methyl ethyl ketone, diethyl ketone or cyclohexanone, the ammonia is used in gaseous form or in solution in water, and the reaction is carried out at a temperature of about −20 to 100°C at a pressure ranging from about normal up to an excess pressure of about 10 atmospheres in a solvent selected from the group consisting of hydrocarbons with up to 12 carbon atoms, lower chlorinated hydrocarbons, halogenated derivatives of benzene, and alcohols with from 5 to 10 carbon atoms.

10 Claims, No Drawings

PRODUCTION OF KETAZINES

This invention relates to the production of ketazines.

The ability of oxaziridines to transfer their nitrogen function to other molecules is shared by only a few representatives of this class of compounds [Chem. Ber. 97 (1964) 2521; Chem. Ber. 100 (1967) 2600]. In the reaction of 3,3-methylethyloxaziridine with aniline, it was possible after a reaction time of 2 days to isolate phenyl hydrazine in a yield of 22%. [Z. Chem. 3, 190 (1963)].

By contrast, nothing is known of amination reactions involving N-unsubstituted 3,3-diorganyl oxaziridines and ammonia.

It has now surprisingly been found that the reaction of 3,3-diorganyl oxaziridines with ammonia and ketones can lead directly to ketazines. Specifically, ketazines of the formula

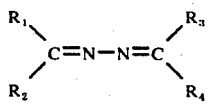

in which
R$_1$, R$_2$, R$_3$ and R$_4$ each independently is alkyl, cycloalkyl or aralkyl with up to 12 carbon atoms, or optionally substituted aryl with up to 10 carbon atoms, at most two of R$_1$, R$_2$, R$_3$, and R$_4$ being aryl, or
R$_1$ + R$_2$ and R$_3$ + R$_4$ individually is alkylene of 5 to 10 carbon atoms,
are prepared by reacting at 3,3-diorganyl oxaziridine of the formula

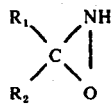

with ammonia in the presence of a ketone of the formula

The radicals R$_1$ to R$_4$ preferably represent linear or branched alkyl radicals with from 1 to 4 carbon atoms, such as, for example methyl, ethyl, propyl, i-propyl or butyl; cycloalkyl radicals with from 5 to 7 carbon atoms such as, for example, cyclopentyl or cyclohexyl; aralkyl radicals with from 7 to 9 carbon atoms, for example benzyl; alkylene radicals with from 5 to 7 carbon atoms such as, for example, pentamethylene or hexamethylene; or aryl radicals with from 6 to 9 carbon atoms such as, for example, phenyl, p-chlorophenyl, p-methyl phenyl or o-methoxy phenyl.

The advantages of the process according to the invention over conventional processes for the production of azines include the high, in some cases, quantitative yields obtained after short reaction times, and the fact that the reaction mixtures can readily be worked up into the ketazines, while all the other reactants can be recycled to the process. The reaction takes place in accordance with the following equation (1):

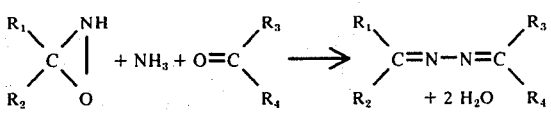

cas (1)

Oxaziridines of formula (II) suitable for use in the process according to the invention are, for example, 3,3-dimethyl oxaziridine 3,3-methyl ethyl oxaziridine, 3,3-diethyl oxaziridine, 3,3-methyl phenyl oxaziridine 3,3-methyl isopropyl oxaziridine, 3,3-cyclohexyl-n-propyl oxaziridine 3,3-hexamethylene oxaziridine, and the like. They are produced by known methods [Chem. Ber. 100, 2593 (1967); Angew. Chemie. 76, 197 (1964); Chem. Ber. 99, 3233 (1966)].

The following ketones may for example, be used as ketones corresponding to formula (III): acetone, methyl ethyl ketone, diethyl ketone, methyl isopropyl ketone, methyl phenyl ketone, cyclohexanone and cycloheptanone. As can be seen from equation (1), it is possible to obtain symmetrical and asymmetrical ketazines when, on the one hand, the radicals R$_3$ and R$_4$ are the same as R$_1$ and R$_2$ and, on the other hand, when the radicals R$_3$ or R$_4$ are different from R$_1$ and R$_2$.

The ketones can be used in pure form or in solution in an organic solvent.

Ammonia may be used in gaseous form or in the form of concentrated aqueous solutions containing about 5 to 30% by weight of NH$_3$. The reaction is best carried out in solution because the oxaziridines are unstable in pure form. In general, it is possible to use solvents which are stable with respect to the reactants and those solvents used in the production of the oxaziridines.

Suitable solvents are linear or branched hydrocarbons with up to 12 carbon atoms, lower halogenated hydrocarbons or halogenated derivatives of benzene and alcohols with from 5 to 10 carbon atoms. Examples of suitable solvents include benzene, toluene, xylenes, methylene chloride, chloroform, carbon tetrachloride, 1,2-dichloroethane, chlorobenzene, chlorotoluene, amyl alcohol, hexanol, 2-ethyl hexanol, 3,5,5-trimethyl hexanol or decanols.

The process according to the invention is carried out by reacting the oxaziridines of formula (II) in solution in an organic solvent with ammonia in the presence of the ketones of formula (III). The reaction is carried out by introducing gaseous ammonia or ammonia in the form of an aqueous solution into a mixture of oxaziridines (II) and ketones (III), or by introducing ammonia and ketone (III) simultaneously into the oxaziridine solution, or by introducing only the ammonia to begin with and then, on completion of the reaction, the ketone (III) into the reaction mixture. The reaction may be carried out under normal pressure, or under an excess pressure of up to about 10 atmospheres if it is necessary to keep the excess ammonia in solution.

The molar ratio of oxaziridine (II) to ammonia can be in the range of about 1 : 1 to 1 : 100, a molar ratio of about 1 : 2 to 1 : 20 being preferred.

The molar ratio of oxaziridine (II) to ketone (III) can be in the range of about 1 : 0.5 to 1 : 20, although a molar ratio of about 1 : 1 to 1 : 5 is preferred. The concentration of oxaziridine in organic solvents can be about 0.01 to 10 moles per liter and is preferably about 0.1 to 5 moles per liter, the range from 0.5 to 3 moles per liter being the most suitable.

The reaction temperature can be in the range of about −20° to +100°C, temperatures in the range of about 0°C to 70°C being preferred. The reaction temperature is governed primarily by the boiling point of the solvent and by the concentration of ammonia.

The reaction may be carried out continuously or in batches and is best carried out immediately after preparation of the oxaziridine.

The ketazines obtained by the process according to the invention can be used for the production of hydrazine hydrate by hydrolysis using known methods, or, by means of acids, for the production of hydrazine salts accompanied by liberation of the ketones.

The process according to the invention is illustrated by the following Examples:

Preparation of Starting Material 50 ml of NaOH-free aqueous chloramine solution, containing 0.044 mole of chloramine, are added with vigorous stirring to a mixture of 100 ml of 1 N NaOH (0.1 mole), 100 ml of methylene chloride and 10 ml of acetone (0.137 mole). After 30 seconds, the organic phase contains 43.5% of the theoretical amount of 3,3-dimethyl oxazirane.

$^1$H-NMR (CH$_2$Cl$_2$) : 8.41 and 8.58 (CH$_3$)

For concentration 350 ml of methylene chloride solution containing 0.0588 mole of 3,3-dimethyl oxyziridine are dried over sodium sulfate, and concentrated under normal pressure to approximately 10 ml in a 40 cm Raschig column with a reflux ratio of 3 : 1. A solution containing approximately 1.8 moles of 3,3-dimethyl oxaziridine per liter of methylene chloride together with unreacted acetone is obtained for a distillation yield of 78%. Acetone-free oxaziridine solutions are prepared by distillation in the presence of a higher-boiling solvent, for example 1,2-dichloroethane.

EXAMPLE 1

An oxaziridine solution in methylene chloride or 1,2-dichloroethane, prepared as described above, is added dropwise over a period of 15 to 20 minutes at T°C to a mixture of 50 ml of concentrated ammonia (0.735 mole) and 5ml of acetone (0.068 mole), followed by stirring for 30 minutes. The reaction is actually over on completion of the dropwise addition. The starting material can no longer be detected. The dimethyl ketazine formed is detected by titration in each of the phases. The results are set out in Table 1.

Table 1

| Concentration of 3,3-dimethyl oxaziridine in moles per liter | Solvent/ml | Reaction time, mins | Yield of dimethyl ketazine in % | Temperature, °C |
|---|---|---|---|---|
| 0.9 | CH$_2$Cl$_2$/10 | 15 | 100 | 0 |
| 0.9 | CH$_2$Cl$_2$/10 | 15 | 95.1 | 40 |
| 0.64 | C$_2$H$_4$Cl$_2$/20 | 15 | 97 | 10 |
| 0.64 | C$_2$H$_4$Cl$_2$/20 | 20 | 87 | 30 |

EXAMPLE 2

Gaseous ammonia is introduced at a temperature of 20°C up to the saturation point into 250 ml of a solution of the oxaziridines in toluene containing 0.05 mole of ketone. The gaseous ammonia is introduced at a rate of 20 liters per hour. After the slightly exothermic reaction has abated, the ketazines formed are quantitatively determined by titration. The results are set out in Table 2 below.

EXAMPLE 3

25 ml of concentrated ammonia (0.37 mole) are added to 200 ml of a methylene chloride solution containing 28.5 millimoles of pentamethylene oxaziridine and 50 millimoles of cyclohexanone. After 1 hour, both phases together contain 24.3 millimoles of pentamethylene ketazine, corresponding to a yield of 85.4%.

Table 2

| Ketone | Oxaziridine used | Quantity in m mol/250 ml | Ketazine obtained | Yield of ketazine in % |
|---|---|---|---|---|
| Diethyl ketone | 3,3-diethyl | 20.4 | diethyl | 81.4 |
| Methyl isopropyl ketone | 3,3-methyl isopropyl | 33.6 | methyl isopropyl | 99.8 |
| Cyclohexanone | 3,3-pentamethylene | 23.3 | pentamethylene | 81.1 |

It will be appreciated that the instant specification and examples are set forth by way of illustration and not limitation, and that various modifications and changes may be made without departing from the spirit and scope of the present invention.

What is claimed is:

1. A process for the production of a ketazine of the formula

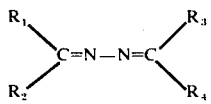

in which
R$_1$, R$_2$, R$_3$ and R$_4$ each independently is an alkyl, cycloalkyl or aralkyl radical with up to 12 carbon atoms, or an aryl radical with up to 10 carbon atoms, at most two of the radicals R$_1$, R$_2$, R$_3$ and R$_4$ being aryl radicals, or
R$_1$ + R$_2$ and R$_3$ + R$_4$ individually is an alkylene radical with from 5 to 10 carbon atoms,
which comprises reacting a 3,3-diorganyl oxaziridine of the formula

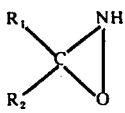

with ammonia in the presence of a ketone of the formula

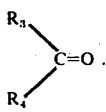

2. A process as claimed in claim 1, wherein the 3,3-diorganyl oxaziridine is 3,3-dimethyl oxaziridine, 3,3-methyl ethyl oxaziridine, 3,3diethyl oxaziridine or 3,3-pentamethylene oxaziridine.

3. A process as claimed in claim 1, wherein the ketone is acetone, methyl ethyl ketone, diethyl ketone or cyclohexanone.

4. A process as claimed in claim 1, wherein the ammonia is used in gaseous form or in solution in water.

5. A process as claimed in claim 1, wherein the reaction is carried out in the presence of an organic solvent partly miscible or immiscible with water.

6. A process as claimed in claim 5, wherein the solvent is selected from the group consisting of hydrocarbons with up to 12 carbon atoms, lower chlorinated hydrocarbons, halogenated derivatives of benzene, and alcohols with from 5 to 10 carbon atoms.

7. A process as claimed in claim 1, wherein the reaction is carried out at a temperature of about −20 to 100°C.

8. A process as claimed in claim 1, wherein the reaction is carried out under a pressure ranging from about normal up to an excess pressure of about 10 atmospheres.

9. A process as claimed in claim 2, wherein the ketone is acetone, methyl ethyl ketone, diethyl ketone or cyclohexanone, the ammonia is used in gaseous form or in solution in water, and the reaction is carried out at a temperature of about −20 to 100°C at a pressure ranging from about normal up to an excess pressure of about 10 atmospheres in a solvent selected from the group consisting of hydrocarbons with up to 12 carbon atoms, lower chlorinated hydrocarbons, halogenated derivatives of benzene, and alcohols with from 5 to 10 carbon atoms.

10. A process as claimed in claim 1 wherein the aryl radical is selected from the group consisting of phenyl, p-chlorophenyl, p-methylphenyl, and o-methoxyphenyl.

* * * * *